United States Patent [19]

Kigasawa et al.

[11] Patent Number: 4,952,560

[45] Date of Patent: Aug. 28, 1990

[54] OINTMENT BASE

[75] Inventors: Kazuo Kigasawa; Hideaki Ohtani; Makoto Tanaka; Shigeru Hayashida, all of Tokyo, Japan

[73] Assignee: Takeda Chemical Industries, Ltd., Osaka, Japan

[21] Appl. No.: 183,307

[22] Filed: Apr. 11, 1988

Related U.S. Application Data

[63] Continuation of Ser. No. 720,402, Apr. 5, 1985, abandoned.

[30] Foreign Application Priority Data

Apr. 5, 1984 [JP] Japan .................................. 59-66711
Feb. 13, 1985 [JP] Japan .................................. 60-24394

[51] Int. Cl.$^5$ ...................... A61K 37/02; A61K 47/38
[52] U.S. Cl. .......................................... 514/2; 514/773; 514/774; 514/777; 514/781; 514/801; 514/947; 514/969
[58] Field of Search .................... 514/947, 2, 801, 969, 514/773–781

[56] References Cited

U.S. PATENT DOCUMENTS

| | | | |
|---|---|---|---|
| 1,663,323 | 3/1928 | Whatmough | 252/180 |
| 3,395,236 | 7/1968 | White | 514/801 |
| 3,991,184 | 11/1976 | Kludas et al. | 514/801 |
| 4,454,159 | 6/1984 | Musher | 514/801 |

FOREIGN PATENT DOCUMENTS

| | | | |
|---|---|---|---|
| 43738 | 1/1982 | European Pat. Off. | 514/947 |
| 4432 | 1/1984 | Japan | 514/2 |
| 506415 | 5/1976 | U.S.S.R. | 514/801 |
| 200036 | 7/1923 | United Kingdom . | |

OTHER PUBLICATIONS

Huc et al., cited in Chem. Abstracts, vol. 95:225469w, (1981).
Batasheva, cited in Chem. Abstracts, vol. 87:206442a, (1977).
Drug Design, vol. IV, (1973), pp. 107–117.
Abstract of JP5920212.
Tazinazo et al., cited in Chem. Abstracts, vol. 89:204219a, 1978.
Balsam et al., eds Cosmetics: Science and Technology, 1972, p. 216.

*Primary Examiner*—Jacqueline Stone
*Attorney, Agent, or Firm*—Antonelli, Terry, Stout & Kraus

[57] ABSTRACT

An ointment base for external use is provided which contains a water-soluble protein and monohydric alcohol or/and oleginous substance and additionally contains a wetting agent. The present ointment base offers a markedly improved percutaneous absorption of drugs, as compared with the conventional ointment bases.

8 Claims, No Drawings

OINTMENT BASE

This application is a continuation of application Ser. No. 720,402 filed Apr. 5, 1985, abandoned.

This invention relates to an ointment base which contains a water-soluble protein and monohydric alcohol or/and oleaginous substance and further contains a wetting agents.

An ointment is a semisolid pharmaceutical preparation, in the form of a gel or cream, for local administration of a drug. It is applied to the skin so that the drug can be released and permeate the skin. Therefore, the most important quality of an ointment is that it delivers the incorporated drug onto the skin surface rapidly and positively so that it may find its way into the lesion. Another requisite of an ointment is that it is use-worthy in terms of irritation to the skin, feeling of use, and stability of the preparation. To satisfy these requirements, a variety of ointment bases have heretofore been proposed.

Japanese Kokai Sho No. 56-71025 discloses hydrophilic and good water-holdable base for plaster containing gelatin, polyvinylalcohol or polyvinylpyrrolidone, sodium polyacrylate, carboxyvinyl polymer, polyhydric alcohol such as glycerin and water, in addition to, for example, methyl salicylate. Japanese Kokai Sho No. 55-9046 discloses a skin coating composition such as a cosmetic carrier containing chondroitin sulfuric acid or sulfate, gelatin, polyvalent alcohol such as glycerin and water, in addition to, for example, vitamin $B_6$. However, these are not satisfactory yet. Particularly there are many problems left unsolved as for example, the skin acts as a barrier to the absorption of the drug. One cannot place much expectations on the systemic effects of drugs administered by the percutaneous route, because difficulty is encountered in the release of the drug and its penetration, and bioavailability of such preparations is remarkably poor in comparison with that of corresponding oral preparations. It is for these reasons that the advent of an ointment base free from the above-mentioned disadvantages has been awaited.

In the above technical situation, the present inventors have found, after intensive researches to develop an ointment base for external use which is free from said drawbacks, that the use of an ointment base containing a water-soluble protein and alcohols or/and oleaginous substance results in a marked improvement in the percutaneous absorption of drugs. Further studies have followed the findings, and ultimately this invention has been established. No other available ointment base offering such an improved percutaneous absorption of drugs as the present preparation has been known.

Thus, this invention relates to an ointment base characterized by containing (1) a water-soluble protein having the property to promote percutaneous absorption of drugs, (2) monohydric alcohol or/and oleaginous substance and a wetting agent.

Any water-soluble protein (1) may be employed as long as the protein is able to promote percutaneous absorption of the drug used. Such protein may be a naturally occurring one or a non-natural one. The former includes animal protein and vegetable protein, while the latter include peptides artificially derived or synthesized. Although there are fields of technology where a sharp distinction is made between peptide and protein, peptides are included in the category of the protein for the purposes of this invention, when we take its action and effect into account.

Examples of said animal proteins include gelatin, solubilized collagen, casein (and its sodium salt), glue, and their hydrolysates. The gelatin and solubilized collagen include the soluble proteins obtainable by acid or alkali hydrolysis or hot water treatment of proteins from animal bones or skins, and the products derived therefrom by suitable chemical modifications (for example, succinylation, maleylation, phthalation), and they range from about tens of thousand to hundreds of thousand in molecular weight. Typical of said vegetable proteins are soybean protein (for example, the protein obtainable by sedimentation and enzymatic treatment of the water-soluble fraction of solvent-extracted soybean cake) and soybean casein. The peptides mentioned above include the peptides obtainable by homo- or hetero-condensation of amino acid by such techniques as chemical synthesis, fermentation or semi-synthesis, and their molecular weight are generally in the range of a few hundred to tens of thousand. As such, the constituent amino acids of the peptides may be neutral, basic or/and acidic, optically active or/and racemic, natural or/and synthetic. In accordance with this invention, one or more, preferably one or two of such water-soluble proteins can be employed. For instance, gelatin can be used either alone or in admixture with casein, etc. Moreover, in consideration of promotant effects on drug absorption, compatibility or dispersability with other components, ease of availability, etc., gelatin, solubilized collagen, casein, soybean protein, etc. are generally utilized with advantage.

The amount of said water-soluble protein need only be that which helps accomplish the objects of this invention, and preferably that which ensures a sufficient promoting effect on the percutaneous absorption of the drug used. For this purpose, the water-soluble protein is in many instances used in an amount substantially equal to or surpassing the amount of the drug. The protein is used generally in a proportion of about 0.5 to 30 weight percent, preferably about 0.5 to 20 weight percent, more preferably about 1 to 10 weight percent, based on the whole ointment base of this invention.

The monohydric alcohols mentioned herein-before (2) may be such alcohols that has mainly the function as solvents, more specifically having the function to increase compatibility or dispersability of the components contained. Examples of the said alcohols include monovalent alcohols having carbon number 2 to 4, for example, lower alcohol such as ethanol, isopropanol and butanol. In general, ethanol is preferred. When such a solvent is used, its amount need only be that which is sufficient to accomplish the aforesaid object, and it is usually 1 to 45 weight percent, preferably 5 to 40 weight percent, more preferably 5 to 35 weight percent, based on the ointment base of this invention.

Examples of the oleaginous substance mentioned hereinbefore (2) include fatty acid esters, aliphatic higher alcohols, paraffin oil, lanolin oil, silicone oil, Plastibase ® (tradename of Squibb and Sons Corp., U.S.A.)

Fatty acid esters mentioned hereinbefore may be the synthetic or naturally occurring esters of aliphatic carboxylic acids and aliphatic alcohols. The said aliphatic carboxylic acids include saturated or unsaturated aliphatic mono- or di-carboxylic acids, typical of which are lower or higher fatty acids having 2 to 24 carbon atoms, and, in particular, medium or higher fatty acids having 6 to 20 carbon atoms are preferred. Examples of such fatty acids are as follows: acetic acid, propionic acid, hexanoic acid, capric acid, caprylic acid, octanoic acid, dioctanoic acid, adipic acid, sebacic acid, palmitic acid, stearic acid, oleic acid, linolic acid, linolenic acid and myristic acid.

Aliphatic alcohol moiety for the oleaginous substance mentioned hereinbefore include saturated or unsaturated aliphatic monool and triol having 1 to 30 carbon atoms, preferably 1 to 20 carbon atoms and polyol having 4 to 8 hydroxyl groups. The said monool includes straight chain or branched alcohols, for example methanol, ethanol, propanol, butanol, hexanol, octanol, decanol, hexadecanol, octyldodecyl alcohol, palmityl alcohol, stearyl alcohol and myristyl alcohol. Typical of the said triol is glycerin and typical of the said polyol includes sorbitol or sorbit and saccharose. As the aforesaid ester of aliphatic carboxylic acid and aliphatic alcohol, esters of which all carboxylic groups and alcoholic hydroxy groups participate in the ester formation (perfect ester) are preferred, but in some cases, it may be the esters of which one carboxylic group in the molecule of aliphatic dicarboxylic acid or/and a part of the hydroxy groups in the molecule of tri-(poly-)ol are free or partial ester. The said ester may be a mixed ester. Among others, glycerides, particularly tri-glycerides, of medium or higher fatty acid having 6 to 20 carbon atoms, perfect ester of medium or higher fatty acid having 6 to 20 carbon atoms and aliphatic monool having 1 to 20 carbon atoms, or a partial ester of the former with polyol are preferably used. The examples of the aforesaid fatty acid esters are given below: isopropyl myristate, octyldodecyl myristate, myristyl myristate, isopropyl palmitate, butyl stearate, decyl oleate, diisopropyl adipate, diethyl sebacate, hexyldecyl dioctate, sorbitan monopalmitate, succharose fatty acid ester, triacetin, di- or triglyceride caprylate, di- or tri-glyceride caprate, mixed trigriceride comprising caprylic acid and capric acid, di- or tri-glyceride oleate, di- or tri-glyceride linolate and mixed glyceride comprising oleic acid and linolic acid.

As the aliphatic esters mentioned herein-before, either that in the almost pure state as in the case of synthetic product or that in the state admixed with other substances as in the case of naturally-occurring product may be used without problem. In the case of the former, the aforesaid substance is used as it is, while in the latter case, natural oils and fats, for example, such animal oils as lard, beef tallow or spermaceti, or such vegetable oils as soybean oil, sesame oil, cotton seed oil, palm oil, olive oil, castor oil or beeswax, are used.

Typical aliphatic higher alcohols mentioned hereinbefore are saturated and unsaturated aliphatic alcohols having 14 to 20 carbon atoms, for example, cetanol or palmityl alcohol, stearyl alcohol, oleyl alcohol and hexadecyl alcohol.

Paraffin oil mentioned hereinbefore includes those made mainly of the mixture of paraffins having 15 or more carbon atoms, for example, fluid paraffin, vaseline including white vaseline, squalane and squalene, of which fluid paraffin, white vaseline, squalane, etc. are preferably used.

Silicone oil mentioned hereinbefore includes admixture of the polymers of dimethylsiloxane, for example, dimethylpolysiloxane and its alkyl ester, methylphenylpolysiloxane or glycol methylsiloxane.

Lanolin oil mentioned hereinbefore includes lanolin, lanolin wax, hydrogenated or reduced lanolin and its polymer with ethylene oxide, of which lanolin is generally preferred.

Main chemical composition of the said lanolin is usually as follows: 30 to 35 weight percent of alcohols, for example, cetyl alcohol, lanolin alcohol and carnaubyl alcohol, 15 to 20 weight percent of cholesterins, for example, cholesterin, isocholesterin and metacholesterin and 45 to 55 weight percent of fatty acids, for example, acetic acid, butyric acid, caproic acid, myristic acid, stearic acid and lanostearic acid.

As the oleaginous substance mentioned hereinbefore, those having either one of the functions owing to covering the skin, for example, protecting from infiltration or stimulation of foreign matters from outside, or modifying the skin or eschar, are used. Those giving less stimulation to skin and having better dispersability and compatibility with other components are preferred. As such oleaginous substance, the products in liquid, paste or wax state are available, and the product in either of the said states may be used without problem. In general, it will be convenient to use the products sold on the market.

For the purpose of this invention, one or more, preferably one to four of the afore-mentioned oleaginous substances may be used. The amount of said oleaginous substance to be used need only be that which is sufficient to accomplish the objects of this invention, and the amount generally used is 0.5–30 weight percent, preferably 0.5 to 25 weight percent, more preferably about 1 to 20 weight percent, based on the whole ointment base of this invention.

The ratio of composition of the said alcohols to oleaginous substances when they are co-used cannot be mentioned specifically, but usually the ratio of alcohols: oleaginous substance is about 1:0.02 to 10, preferably 1:0.03 to 5 by weight.

Any wetting agent (3) is used as long as it contributes to improve quality characteristics such as the moisture retentivity, spreadability, gloss and feeling of the ointment. Examples of wetting agent include polyhydric alcohols and amino acids as representative examples. The polyhydric alcohols include glycols, triols and polyols having 4 to 6 alcoholic hydroxyl groups, and the amino acids include various amino acids commonly known as natural amino acids. The glycols include alkylene glycols containing 2 to 6 carbon atoms, e.g., ethylene glycol, propylene glycol, butylene glycol, etc.; polyethylene glycol having average molecular weight of about 200 to 8,000, preferably 200 to 6,000, etc.; said triols include glycerin, trimethylolpropane, etc.; and said polyols include sorbitol or sorbit, etc. In particular, the said alkylene glycol, polyethylene glycol, glycerin and sorbitol are preferably used. In the practice of this invention, one or more, preferably one or two of said wetting agents can be used. The proportion of such wetting agent or agents need only be that which satisfies the above-mentioned purpose, and may range generally from about 1 to 35 weight percent and preferably from about 2 to 30 weight percent when water is concomitantly used and generally from about 40 to 90 weight percent and preferably from about 50 to 85 weight percent, more preferably from about 60 to 85 weight percent, based on the whole ointment base of this invention when water is not used.

In the ointment base of this invention, the components heretofore used in the conventional ointment bases may be incorporated in addition to the above-mentioned (1) water-soluble protein, (2) monohydric alcohol or/and oleaginous substance and (3) wetting agent. As such components, thickeners or/and emulsifiers may be used in a composition of several varieties selected according to the intended application. For example, when a thickener is used in addition to said water-soluble protein, generally a gel-like ointment base is obtained, while the use of an emulsifier in addition to said water-soluble protein generally results in a cream-like ointment base. The addition of an emulsifier to the above gel-like base, and of a thickener to the above cream-like base is permissible within the range not in conflict with the objects of this invention.

The above-mentioned thickener is a substance which increases the viscosity of the whole ointment to thereby contribute to the necessary product characteristics such as desirable rheologic properties or improved affinity to the skin. Among examples of such thickener are cellulose derivatives, polysaccharides, carboxyvinyl polymers, polyvinyl alcohol, polyvinylpyrrolidone, etc.

The above-mentioned cellulose derivatives include alkylcelluloses and hydroxyalkylcelluloses, whose average molecular weights are in the range of about 40,000 to 200,000 and whose alkyl moieties contain 1 to 4 carbon atoms, e.g. methylcellulose, ethylcellulose, propylcellulose, methylpropylcellulose, hydroxymethylcellulose, hydroxyethylcellulose, hydroxypropylcellulose, and carboxymethylcellulose and its alkali metal salts, etc. Examples of said polysaccharides include simple polysaccharides such as starch and its derivatives, e.g. carboxymethylstarch, hydroxypropylstarch, dextrin, dextran, chitin alginic acid and its sodium salt, glycogen, Pluran ® (the trademark of Hayashibara in Japan), carrageenan, etc., and complex polysaccharides such as xanthane gum, mannan, pectin and gum arabic. In particular, sodium alginate, carrageenan, xanthane gum are preferred. The above-mentioned carboxyvinyl polymers are those having average molecular weights in the range of about 900,000 to 3,000,000, and include polyacrylic acid, polymethacrylic acid and their alkali metal salts. In particular, sodium polyacrylate is preferably used. To be specific, such commercial products as Hiviswako ® (the trademark of Wako Junyaku in Japan), Carbopol ® (the trademark of Goodrich in U.S.A.), Luviskol ® (trademark of BASF, West Germany), etc. can be advantageously employed. In accordance with this invention, one or more of the thickeners mentioned-above can be employed. Where such a thickener is employed, its amount need only be that which satisfied the above-mentioned purpose of use, and may range generally from about 0.1 to 10 weight percent, and preferably from about 0.5 to 5 weight percent.

The above-mentioned emulsifier is a substance having the property to emulsify or disperse the components evenly into the product base. Generally, the emulsifier is preferably a substance having surface active properties and, therefore, various nonionic, anionic and cationic surfactants can be utilized. Examples of said surfactants include Polysorbate 80, sorbitan fatty acid esters, fatty acid monoglycerides, sucrose fatty acid esters, aliphatic alcohol polyoxyethylene derivatives, fatty acid polyoxyethylene derivatives, polyoxyethylene derivatives of polyhydric alcohol fatty acid esters, sodium laurylsulfate, lecithin, dioctyl sulfosuccinate, etc. In particular, nonionic surfactants such as Polysorbate 80 is preferably used. In place of the above-mentioned emulsifier or concomitantly with the said emulsifier, an appropriate solution auxiliaries, e.g. such organic amines as diisopropanolamine, crotamiton; such amino acids as l-lysine, may be used for the same purpose.

In the practice of this invention, one or more of the above-mentioned emulsifiers are employed. When such emulsifier is employed, its amount need only be that which satisfies the above-mentioned purpose of use, and may range generally from about 0.1 to 5 weight percent and preferably from about 0.5 to 4 weight percent and more preferably from about 0.5 to 3 weight percent, based on the whole ointment base of this invention.

In addition to the above-mentioned components, suitable amount of water may be added for the purpose of ensuring the product characteristics of the ointment base of this invention. The proportion of water is generally about 20 to 80 weight percent, preferably about 35 to 75 weight percent, and more preferably about 40 to 70 weight percent.

Further, in the ointment base of this invention, preservatives and pH controlling agents may be added, if necessary. As such a preservative, publicly known preservatives for conventional ointments for the purpose of preventing degeneration by microorganism or putrefaction, e.g. such parabens as methyl, ethyl, or propyl ester of paraoxy-benzoic acid, sorbic acid, dehydro-acetic acid, etc. may be used. Such a preservative is generally added in an amount of about of 0.05 to 2 weight percent,preferably about 0.1 to 1 weight percent,relative to the whole composition. As an above-mentioned pH controlling agent, substances having the properties mainly to maintain stability of the components, alleviate stimulation or/and maintain drug absorbability of the skin through adjustment of pH, for example, organic acids, e.g. citric acid, lactic acid and tartaric acid or inorganic acids, e.g. hydrochloric acid, sulfuric acid and phosphoric acid or their alkali metal salts may be used. The amount of such pH adjusting agent is generally about 0.1 to 5 weight percent and preferably about 1 to 4 weight percent, relative to the whole amount of the composition.

The present ointment base having the foregoing composition is used for medical and cosmetic uses. When the main purpose of using the base is a medical one, various drugs are added during or after their production according to the intended purposes. There is no limitation on the type of drug that can be used, provided that it can be absorbed percutaneously. Thus, the above-mentioned drug includes both the drugs topically applied for local effects and those administered for systemic effects. The topical drugs include drugs administrated for the purpose of curing diseases on the skin surface or under the skin or for protective conditioning of the skin and display mainly local effects. The drugs for systemic administration are drugs absorbed from the skin surface where they are applied and reach the target tissue or organ via the circulation to display mainly systemic effects. Among such drugs are drugs which display effects on circulatory system, nerve system, endocrine system, respiratory system, metabolic system, urinary system, digestive system, etc., antimicrobial agent, anti-tumor agent, vitamins, antidiabetics, enzymes, Chinese medicines, natural herb extract, etc. More specific examples of such drugs are as follows:

(1) Analgesic antiinflammatory agents: acetaminophen, aspirin, salicylic acid, methyl salicylate, choline salicylate, glycol salicylate, l-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, etc.; (2) steroid antiinflammatory agents: hydrocortizone, prednisolone, dexamethasone, triamcinolone acetonide, fluocinolone acetonide, fludrocortisone acetate, etc.; (3) antihistaminics or antiallergic agents: chlorpheniramine, glycyrrhizic acid, diphenhydramine, periactin, etc.; (4) local anesthetics: benzocaine, procaine, dibucaine, lidocaine, etc.; (5) antimicrobial agents including antibacterial agents, antimycotic agents, antifungal agents and antiviral agents: tetracyclines such as chlortetracycline, penicillins such as ampicillin, cephalosporins such as cefalotin, aminoglycosides such as kanamycin, macrolides such as erythromycin, chloramphenicol, iodine compounds, nitrofrantoin, nystatin, amphotericin, fradiomycin, sulfonamides, pyrrolnitrin, clotrimaxol, etc.; (6) antihypertensive agents: clonidine, α-methyldopa, reserpine, syrosingopine, rescinnamine, cinnarizine, hydralazine, prazosin, etc.; (7) anti-hypertensive diuretics: theophylline, trichlormethiazide, furosemide, tripamide, methylclothiazide, penfluzide, hydrothiazide, spironolactone, metolazone, etc.; (8) cardiacs: digitalis, ubidecarenon, depamine, etc.; (9) coronary vasodilators: nitroglycerin, isosorbitol dinitrate, erythritol tetranitrate, pentaerythritol tetranitrate, dipyridamole, dilazep, trapidil, trimetazidine, etc.; (10) vasoconstrictors: dihydroergotamine, dihydroergotoxine, etc.; (11) β-blockers or antiarrythmic agents: pindolol, propranolol, etc.; (12) calcium antagonists and other drugs for circulatory organs: diltiazem, nifedipine, nicardipine, verapamil, bencyclane, fenprodil tartrate, morcidomine, etc.; (13) anticonvulsants: nitrazepam, meprobamate, phenytoin, etc.; (14) agents for dizziness: isoprenaline, betahistine, scopolamine, etc.; (15) minor tranquilizers: diazepam, lorazepam, flunitrazepam , fluphenazine, etc.; (16) hypnotics and sedatives: phenobarbital, amobarbital, cyclobarbital, etc.; (17) muscle relaxants: tolperisone, baclofen, dantrolene sodium, cyclobenzaprine; (18) autonomic agents: atropine, levodopa, etc.; (19) respiratory agents: codeine, ephedrine, isoproterenol, dextromethorphan, orciprenaline, ipratropium bromide, cromglycic acid, etc.; (20) hormones or antihormones: corticotropin, oxytocin, vasopressin, testosterone, progesterone, estradiol, salivary hormone, thyroid hormone, adrenal hormone, kallikrein, insulin, oxendolone, etc.; (21) vitamins: vitamins A, B, C, D, E and K and derivatives thereof, calciferols, mecobalamin, etc.; (22) antitumor agents: 5-fluorouracil and derivatives thereof, krestin, picibanil, ancitabine, cytarabine, etc.; (23) enzymes: lysozyme, urokinaze, etc.; (24) Chinese medicines or herb extracts: liquorice, aloe, Sikon (Lithospermi Radix), etc.; (25) antiulcer agents: allantoin, aldioxa, alcloxa, N-methylscopolamine methyl sulfate, etc.; (26) prostaglandins; (27) antidiabetics; etc.

The drugs mentioned above can be used in combination if required. Moreover, the above drugs may be used either in the free form or, if capable of forming salts, in the form of a salt with a suitable acid or base. If the drugs have a carboxyl group, their esters can be employed. The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid, sulfuric acid. The base may be an organic base, for example, ammonia, triethylamine, or an inorganic base, for example, sodium hydroxide, potassium hydroxide. The esters mentioned above may be alkyl esters, aryl esters, aralkyl esters, etc. Among the said drugs, particularly those which act upon circulatory system, nervous system, endocrine system, respiratory system, antimicrobial agents, enzymes etc. are preferably used as the drugs of this invention.

As mentioned hereinbefore, this invention can be applied to any kind of drugs but the advantage of this invention is particularly remarkable for drugs which indicate practically no or little percutaneous absorption when administered alone, drugs of which bioavailability is low when administered orally, e.g. drugs of which bioavailability is less than 80 percent, drugs causing many side effects, drugs which require administration by injection because of their decomposition by digestive fluid or drugs which are easily effected by initial passage through liver.

The concentration of the drug need only be that which exhibits the expected clinical effect, and in many instances ranges from 0.01 to 15 weight percent, preferably 0.05 to 10 weight percent, more preferably 0.05 to 5 weight percent, based on the weight of the whole composition. The dosage is adjusted according to the type of drug, object of medication, age and body weight of the patient, stage of disease, etc.

When the ointment base of this invention is used for medical purpose, the ointment can be manufactured by adding the above-mentioned drugs to the ointment base of this invention as the effective component. Thus obtained ointment can be applied in a necessary amount to the skin at various parts of the human body according to the purpose of use. For example, for the local treatment of an injury, skin ulcer, myalgia arthritis or arthritis of joint, etc., the above medicated base may be applied directly to the affected site or to the vicinity thereof. For systemic therapy for some organ or other within the body, it is preferably applied to an area from which the drug may be more readily absorbed, e.g. where the horny layer is not well developed. In cosmetic applications, the ointment base of this invention either as it is or as containing a suitable drug selected from among those mentioned or/and further containing the known cosmetic ingredients, can be used for such purposes as cleansing the skin, as a pack, preventing sunburns or rough skin, moisturizing and so forth.

The ointment base of this invention either as it is or as containing the above-mentioned medical or/and cosmetic components is preferably accommodated in sealed containers made of glass, plastic or metal tubing for the sake of convenience in storage and use.

For the production of the ointment base according to this invention, conventional production processes can be utilized with minor modifications. In a typical process, (i) the water-soluble protein and thickener are dissolved in a necessary amount of water, (ii) then substances selected from among said wetting agents, alcohols, emulsifiers, oleaginous substances, etc. are added to the above solution, and (iii) finally the whole mixture is stirred uniformly to give the desired ointment base. The above operation may be performed without addition of water. Generally speaking, when the desired product is a gel-like base, the wetting agent and thickener are mainly used in the above step (ii), while the wetting agent and emulsifier are mainly used when a creamy base is to be produced. The above-mentioned steps (i) through (iii) may be performed at room temperature but some of the steps may be carried out, upon necessity, at a somewhat elevated temperature, for example about 30° C. to 80° C. and preferably about 30° C. to 60° C. at a part of the process. In many cases, it is rather advantageous from procedural points of view to conduct the process at slightly elevated temperatures. When a drug or the like is added, it is preferably done in the above-mentioned step (ii).

The method for production of the ointment base of this invention will be described in further detail by way of the following examples.

EXAMPLE 1

According to the formula given in Table 1, (1) 3 g of gelatin was put in 29.5 g of purified water and dissolved by warming at 50° C.;

(2) 2 g of hydroxyethylcellulose was dissolved in 20 g of purified water;

(3) 0.5 g of sodium polyacrylate was dissolved in 10 g of purified water;

(4) 30 g of ethanol and 4 g of 1,3-butylene glycol were mixed together;

(5) the solution (2) and solution (3) were added to the solution (1) and the mixture was stirred at 50° C. using a homomixer to give a homogenous preparation; and (6) the mixture (4) was added to the above mixture (5) and the whole mixture was stirred in a homomixer at 50° C. to give a homogenous preparation.

The above procedure gave a gel-like ointment base.

Separately, the same procedure as above was followed additionally using 1 g of ifenprodil tartrate in the above-mentioned step (4), whereby an ointment was obtained.

EXAMPLES 2–21

According to the formula of Table 1 and by the same procedure as Example 1, a gel-like ointment base was prepared. Separately, in the following examples, ointments were prepared using the respective drugs shown below.

Example 2: 0.5 g of prazosin hydrochloride, 0.05 g of clonidine hydrochloride or 0.5 g of clidanac;

Example 3: 0.5 g of pindolol;

Example 4: 1.0 g of indomethacin;

Example 5: 1.0 g of pentazocine hydrochloride or 1.0 g of dipyridamole;

Example 17: 1.0 g of ifenprodil tartrate.

TABLE 1

| Material/Example | 1 | 2 | 3 | 4 | 5 | 6 | 7 | 8 | 9 | 10 | 11 |
|---|---|---|---|---|---|---|---|---|---|---|---|
| Gelatin | 3 | 3 | 4 | 3 | 3 | 1.5 | 2 | 3 | 3 | 3 | 4 |
| Casein sodium | | | | | | | | | | | |
| Soybean protein | | | | | | | | | | | |
| Hydroxyethylcellulose | 2 | 1.7 | 2 | 1.7 | 1.7 | | 1 | | 1.7 | 1.7 | |
| Methylcellulose | | | | | | | | 1 | | | |
| Sodium alginate | | | | | | | | | | | 1 |
| Sodium polyacrylate | 0.5 | | | | | | | | | | |
| Polyvinyl alcohol | | | | | | | | | | | |
| Glycerin | | 4 | 4 | 4 | 4 | 4 | 4 | 4 | 10 | 10 | 2 |
| Propylene glycol | | | | | | | | | 5 | | 2 |
| 1,3-butylene glycol | 4 | | | | | | | | | | |
| Sorbit solution (70%) | | | | | | | | | | 5 | |
| Isopropyl myristate | | | | | | | | | | | 1 |
| Medium-chain fatty acid triglyceride (Note 1) | | | | | | | | | | | |
| Ethanol | 30 | 30 | 30 | 35 | 30 | 30 | 30 | 30 | 30 | 10 | 30 |
| Water | 59.5 | 60.8 | 59.5 | 55.3 | 60.3 | 64.5 | 63 | 62 | 50.3 | 70.3 | 60 |

| Material/Example | 12 | 13 | 14 | 15 | 16 | 17 | 18 | 19 | 20 | 21 |
|---|---|---|---|---|---|---|---|---|---|---|
| Gelatin | 3 | 3 | 3 | 6 | | | | | | |
| Casein sodium | | | | | 20 | 10 | 10 | 10 | 10 | 10 |
| Soybean protein | | | 5 | | | | | 10 | | |
| Hydroxyethylcellulose | | 1 | 1.7 | 1.7 | | 2 | | 2 | 2 | 3 |
| Methylcellulose | | | | | | | 2 | | | |
| Sodium alginate | 1 | | | | | | | | | |
| Sodium polyacrylate | 0.5 | 0.5 | | | | | | | | 0.5 |
| Polyvinyl alcohol | | 1 | | | | | 1 | | | |
| Glycerin | | 4 | 4 | 4 | | | | 4 | | 4 |
| Propylene glycol | | | | | | | | | 2 | |
| 1,3-butylene glycol | 4 | | | | 10 | 4 | 4 | | | |
| Sorbit solution (70%) | | | 1 | | | | | | 4 | |
| Isopropyl myristate | | | | | | | 1 | | | |
| Medium-chain fatty acid triglyceride (Note 1) | 1 | | | | | | | | | |
| Ethanol | 30 | 30 | 30 | 30 | 30 | 30 | 30 | 20 | 30 | 30 |
| Water | 60.5 | 60.5 | 55.3 | 58.3 | 40 | 53 | 52 | 54 | 52 | 52.5 |

Note 1 ODO ® (mixed caprylic-capric acid (75:25) triglyceride, manufactured by Nisshin Seiyu Kabushiki Kaisha in Japan)
Note 2 All amounts are by weight (g).

TABLE 2

| Material/Example | 22 | 23 | 24 | 25 | 26 | 27 | 28 | 29 | 30 |
|---|---|---|---|---|---|---|---|---|---|
| Gelatin | 3 | 10 | 10 | 10 | 10 | 5 | 4 | 4 | 3 |
| Casein sodium | | | | | | | | | |
| Soybean protein | | | | | | | | | |
| Hydroxyethylcellulose | 1 | | | | | | | | 2 |

TABLE 2-continued

| | Note 3 | | | | | | | | |
|---|---|---|---|---|---|---|---|---|---|
| Methylcellulose | | | | | | 1 | | | |
| Polyvinylpyrrolidone | | | | | | | 2 | | |
| Glycerin | | 2 | | | | | | | |
| Propylene glycol | | | | | 10 | 2 | | | |
| 1,3-butylene glycol | 10 | 10 | 8 | 10 | 10 | | 8 | 10 | 10 |
| Sorbit solution (70%) | | | | | | | | | |
| Isopropyl myristate | | | | | 10 | | | | |
| Octyldodecyl myristate | | | 10 | 10 | | 10 | | 10 | |
| Medium-chain fatty acid triglyceride (Note 1) | | | | | | | | | |
| Cetanol | 0.5 | 1.5 | 1.5 | 1.5 | 1.5 | 1.5 | 1.5 | 1.5 | |
| Liquid paraffin | 10 | 10 | | | | | | | 10 |
| White vaseline | | | 10 | | | | | | |
| Emulsifier (Note 2) | 1 | 1 | 1 | 1 | 1 | 1 | 1 | 1 | 1 |
| Paraben | 0.1 | 0.2 | 0.2 | 0.2 | 0.3 | 0.1 | 0.2 | 0.2 | 0.2 |
| Water | 73.9 | 67.3 | 67.3 | 66.3 | 67.2 | 72.4 | 72.3 | 70.3 | 73.8 |

| Material/Example | 31 | 32 | 33 | 34 | 35 | 36 | 37 | 38 | 39 |
|---|---|---|---|---|---|---|---|---|---|
| Gelatin | | | | | | | 12 | 3 | 4 |
| Casein sodium | 10 | 20 | 10 | 10 | 10 | 10 | | | |
| Soybean protein | | | | | 10 | 10 | | | |
| Hydroxyethylcellulose | 1 | | | | 2 | 1 | | | |
| Methylcellulose | | | | | | | | | |
| Polyvinylpyrrolidone | | | | | | | | | |
| Glycerin | | | | | | | 12 | 84.3 | |
| Propylene glycol | | | | | | | | | |
| 1,3-butylene glycol | 10 | 10 | 10 | 10 | 10 | 10 | | | 10 |
| Sorbit solution (70%) | | | | | | | | | |
| Isopropyl myristate | | | | | | | | | |
| Octyldodecyl myristate | | | 10 | 10 | | | | | |
| Medium-chain fatty acid triglyceride (Note 1) | | | | | | | | | |
| Cetanol | 7 | 1.5 | 1.5 | 7 | 12 | 7 | | 1.5 | 1.5 |
| Liquid paraffin | 10 | 10 | | | | | 10 | 10 | |
| White vaseline | | | | | | | | | 10 |
| Emulsifier (Note 2) | 2 | 2 | 2 | 2 | 2 | 2 | 1 | 1 | 1.5 |
| Paraben | 0.2 | 0.2 | 0.2 | 0.2 | 0.2 | 0.2 | 0.2 | 0.2 | 0.2 |
| Water | 59.3 | 56.3 | 66.3 | 60.8 | 53.8 | 59.8 | 64.8 | 0 | 72.8 |

Note 1 The same as Note 1 of Table 1.
Note 2 Composed mainly of sorbitan monostearate, with polyoxyethylene-sorbitan monostearate and sorbit tetraoleate. In Example 39, sodium laurylsulfate was used.
Note 3 All amounts are by weight (g).

TABLE 3

| | Note 2 | | | | | | | | | | |
|---|---|---|---|---|---|---|---|---|---|---|---|
| Material/Example | 40 | 41 | 42 | 43 | 44 | 45 | 46 | 47 | 48 | 49 | 50 |
| Gelatin | 2 | 1 | 1 | 2 | 1 | 1 | 1 | 1.5 | 1.5 | 1.5 | 3.5 |
| Hydroxyethylcellulose | 0.85 | 1 | 1 | 1 | 1 | 2.5 | 2.5 | | | 2.5 | |
| Sodium alginate | | | | | 1 | | | | | | |
| Sodium polyacrylate | | | | | | | | 0.4 | 0.4 | | |
| Hiviswako ® 104 | | | | | | | | 0.3 | 0.3 | | |
| Carrageenan | | 1 | 1 | | | | | | | | |
| Xanthane gum | | | | 1 | | | | | | | |
| Sorbit solution (70%) | | | | | | | | 5 | 5 | | |
| Glycerin | 3 | | | | | 23 | 23 | | | | 3 |
| Butylene glycol | | 15 | 15 | 10 | 10 | | | | | 10 | |
| Ethanol | 25 | 30 | 30 | 30 | 30 | | 5 | | 5 | 30 | 26.3 |
| Diisopropyl adipinate | | | 1.5 | | 1.5 | | | | | | |
| White vaseline | | | | | | 3 | 3 | 3 | 3 | | |
| Medium-chain fatty acid triglyceride (Note 1) | | | | | | 5 | 5 | 5 | 5 | 5 | |
| Sodium citrate | | | | | | 3 | 3 | 3 | 3 | | |
| Diisopropanolamine | | | 0.25 | 0.2 | 0.2 | | | | | | |
| Polysorbate 80 | | | | | | 1 | 1 | 1 | 1 | 1 | |
| Paraben | | | | | | 0.2 | 0.2 | 0.2 | 0.2 | | |
| Water | 68.85 | 50.0 | 51.25 | 53.8 | 56.3 | 60.3 | 55.3 | 79.6 | 74.6 | 49.5 | 66.9 |

Note 1 The same as Note 1 of Table 1.
Note 2 The same as Note 2 of Table 1.

EXAMPLE 22

According to the formula given in Table 2, (1) 3 g of gelatin was put in 54 g of purified water and dissolved by warming at 50° C.;

(2) 1 g of hydroxyethylcellulose was dissolved in the remaining water;

(3) 0.1 g of paraben, 10 g of liquid paraffin and 10 g of 3-butylene glycol were added to a mixture of 0.5 of cetanol and 1 g of emulsifier and the mixture was stirred;

(4) the solution (2) was added to the solution (1) and the mixture was stirred in a homomixer at 50° C. to give a homogenous preparation; and (5) the mixture (3) was added to the mixture (4) and the whole mixture was stirred in a homomixer initially at the same temperature as above until the temperature lowered to about 30° C., whereby a homogenous preparation was obtained.

The above procedure gave a creamy ointment base.

Separately, the same procedure as above was followed additionally using 0.5 g of clidanac in the above-mentioned step (3), to give an ointment.

EXAMPLES 23-39

According to the formula of Table 2 and by the same procedure as Example 22, a creamy ointment base was prepared. Separately, in the following examples, ointments were prepared using the respective drugs shown below.

Example 31: 0.5 g of clidanac; Example 25: 1 g of ifenprodil tartarate; Example 29: 1 g of pentazocine hydrochloride.

EXAMPLE 40

According to the formula given in Table 3 and by the same procedure as Example 1, the objective ointment base was prepared.

Separately, the same procedure as above was followed additionally using 0.3 g of clonidine hydrochloride to give the following three kinds of ointment.

(a) ointment containing clonidine hydrochloride;

(b) ointment containing clonidine hydrochloride and hydroxypropylcellulose in place of hydroxyethylcellulose for the same amount as the latter; and (c) ointment containing clonidine hydrochloride and methylcellulose in place of hydroxyethylcellulose.

EXAMPLE 41

According to the formula given in Table 3, (1) 30 g of purified water was added to 1 g of gelatin and the latter was dissolved by warming (50° C.);

(2) 1 g of hydroxyethylcellulose was dissolved in 10 g of purified water;

(3) 10 g of purified water was added to 1 g of carrageenan to swell the latter;

(4) 30 g of ethanol, 1.5 g of diisopropyl adipate and 15 g of butylene glycol were mixed;

(5) the solution (2) was added to the solution (1) and the whole was stirred in a homomixer under warming;

(6) carrageenan prepared in step (3) was added to the mixture (5) and the whole mixture was stirred in a homomixer under warming; and (7) lastly, the mixture (4) was added to the mixture (6), warming was discontinued and the mixture was stirred in the homomixer, to produce an ointment base.

Separately the same procedure as above was followed additionally using 0.5 g of piroxicam in the above-mentioned step (4), to give an ointment.

EXAMPLE 42

According to the formula given in Table 3, (1) 21.25 g of purified water was added to 1 g of gelatin and the latter was dissolved by warming (50° C.);

(2) 1 g of hydroxyethylcellulose was dissolved in 10 g of purified water;

(3) 10 g of purified water was added to 1 g of karrageenan and the latter was caused to swell;

(4) 0.25 g of diisopropanolamine was dissolved in 10 g of purified water;

(5) 30 g of ethanol and 15 g of butylene glycol were mixed;

(6) the solution (2) was added to the solution (1) followed by addition of (3) and then (4) while warming and stirring at each addition in a homomixer; and (7) lastly, the mixture (5) was added to the mixture (7), warming was discontinued and stirred in a homomixer, to give the ointment base.

Separately the same procedure as above was followed additionally using 0.5 g of piroxicam in the above-mentioned step (4), to give an ointment.

EXAMPLES 43-44

According to the formula given in Table 3 and following the same procedure as Example 41, ointment base and ointment containing 0.5 g of piroxicam were respectively prepared.

EXAMPLE 45

According to the formula given in Table 3, (1) 15.3 g of purified water was added to 1 g of gelatin and the latter was dissolved by warming (50° C.);

(2) 2.5 g of hydroxyethylcellulose was dissolved in 25 g of purified water;

(3) 3 g of sodium citrate was dissolved in 10 g of purified water;

(4) 1 g of Polysorbate 80 was dissolved in 10 g of purified water;

(5) 0.2 g of paraben was dissolved in 23 g of glycerin;

(6) 5 g of medium chain fatty acid tri-glyceride was mixed well with 3 g of white vaseline by warming;

(7) the solution (2) was added to the solution (1) followed by addition of the solutions (3) and (4) and then solution (5) and stirred at each addition while warming at 50° C. in a homomixer; and (8) lastly, the mixture (7) was added to the mixture (7), warming was discontinued and stirred in a homomixer, to give an ointment base.

Separately, the same procedure as above was followed additionally using 1 g of ifenprodil tartrate in the above-mentioned step (5), to give an ointment.

EXAMPLE 46

The same procedure as Example 44 was followed except additionally using 5 g of ethanol in the step (5) of Example 45, to give respectively an ointment base and an ointment (containing 1 g of ifenprodil tartrate).

EXAMPLE 47

(1) 10 g of purified water was added to 0.3 g of Hiviswako ® 104 to swell the latter;

(2) 5 g of purified water was added to 0.4 g of sodium polyacrylate;

(3) 10 g of purified water was added to 1.5 g of gelatin and dissolved by warming at 50° C.;

(4) 3 g of sodium citrate was dissolved in 5 g of purified water and 5 g of sorbitol was added;

(5) 0.2 g of parabens and 1 g of Polysorbate 80 were dissolved in 49.6 g of purified water;

(6) 5 g of medium-chain fatty acid triglyceride was mixed well with 3 g of white vaseline by warming;

(7) the solution (2) was added to the solution (1) and then solutions (3) and (4) were added thereto, followed by addition of the solution (5) by warming at 50° C. and stirring in a homomixer; and (8) lastly, the mixture (6) was added to the mixture (7), warming was discontinued and the mixture was stirred in a homomixer, to give a ointment base.

Separately the same procedure as above was followed additionally using 1 g of ifenprodil tartrate in the above-mentioned step (5), to give an ointment.

EXAMPLE 48

The same procedure as Example 46 was followed except additionally using 5 g of ethanol in the step (5) of Example 47, to prepare respectively an ointment base and an ointment (containing 1 g of ifenprodil tartrate).

EXAMPLE 49

(1) 44.5 g of purified water was added to 1.5 g of gelatin and the latter was dissolved by warming at 50° C.;

(2) 2.5 g of hydroxyethylcellulose was dissolved in 5 g of purified water;

(3) 30 g of ethanol, 10 g of buthylene glycol and Polysorbate 80 were mixed well;

(4) 5 g of medium-chain fatty acid triglyceride was warmed up to 50° C.;

(5) solution (2) was added to solution (1) followed by addition of the mixture (3) by stirring at each addition while warming at 50° C. in a homomixer; and (6) warmed medium-chain fatty acid triglyceride mentioned in (4) above was added to the mixture (5), warming was discontinued and stirred in a homomixer, to give an ointment base.

Separately the same procedure as above was followed additionally using 0.5 g of prazosin hydrochloride, to give an ointment.

EXAMPLE 50

According to the formula of Table 3, (1) 3.5 g of gelatin was added to 66.9 g of purified water by warming (50° C) in a homomixer;

25 (2) 3 g of glycerin was dissolved in 26.3 g of ethanol; and (3) wetted gelatin mentioned in (1) above was cooled to 30° C. and added gradually to the solution (2) and mixed by stirring, to give the objective ointment base.

Separately the same procedure as above was followed additionally using 0.3 g of clidanac in the above-mentioned step (2), to prepare an ointment.

The ointment base of this invention prepared by the above method has great medical and industrial values, for it can be stored in a stable condition, gave a satisfactory feeling of use and, either as it alone or as formulated with the drug or/and other active components, offers the following advantageous characteristics.

(a) The preparation ensures a high percutaneous absorption of the active component drug. Therefore, not only local effects but also the systemic effect which is difficult to obtain with conventional ointments can be expected.

(b) Drugs which would cause side effects, e.g., gastrointestinal disorders, or poor bioavailability when dosed orally or by other methods can be effectively used in an improved manner, e.g. delayed metabolism.

(c) When the treatment regimen calls for several oral intakes a day, the patient may forget or dislike the taking of drug. There also are cases in which many different drugs must be taken in large amounts. In such cases, the ointment base according to this invention ensures many hours of sustained efficacy at the application interval of once or twice daily. Thus, it is easy for the patient to use and for the doctor to control both the disease and drug effect.

The test examples of the ointment base of this invention are given below.

TEST EXAMPLE 1

Drug Release Test

Method (A) The indomethacin-containing ointment (3 g) according to Example 4 was applied onto an artificial membrane (Millipore Filter ® SSWP ∅ 47, Millipore Co. in U.S.A.) positioned to be adjoining to the level of 200 ml of M/15 phosphate buffer (pH 5.5, 37° C.),and the indomethacin released through the artificial membrane into the above buffer was assayed by HPLC (high performance liquid chromatography type ALC/GPC-208 of Waters Corp. U.S.A.). Thus, 1 ml aliquots of the buffer were taken at timed intervals and each was extracted with 5 ml of dichloromethane. The solvent was evaporated from the extract and the residue was dissolved in 0.2 ml of 75% acetonitrile to prepare an assay sample. For HPLC, Nucleosil C18 (Waters Corp. U.S.A.) was used as the column packing and acetonitrile/0.01M potassium dihydrogen phosphate (75:25) as the mobile phase. The flow rate was 2 ml/min. and the absorbance at the UV frequency of 318 nm was measured.

(B) For control purposes, the same experiment was performed using the same quantity of a commercial 1% indomethacin ointment (Idomecin Kowa Gel ®, Kowa Co., Ltd.).

Results

The results are shown in Table 4.

TABLE 4

| | Release of indomethacin (μg/ml) | | | | |
|---|---|---|---|---|---|
| | Time (min.) | | | | |
| | 5 | 15 | 30 | 60 | 90 |
| (B) Commercial ointment | 0.16 | 0.32 | 0.70 | 1.68 | 2.66 |
| (A) Example 4 | 0.40 | 1.31 | 2.14 | 3.59 | 4.55 |

The above results indicate that as compared with the conventional ointment, the ointment base according to this invention ensures a release of drugs which is quicker and about twice as much.

TEST EXAMPLE 2

Pressor reaction inhibiting effect of prazosin hydrochloride-containing preparation Method (A) The prazosin hydrochloride-containing ointment of Example 2 was applied onto the depilated back of male SD rats (b. wt. 200–300 g, in groups of 6 to 8 rats) and the application site was covered with a tape.

(B) A suspension of prazosin hydrochloride in 1% gum arabic suspension was orally administered.

The dosage for both treatment groups was 20 mg/kg once daily and the treatment was carried out for 3 consecutive days. Twenty-four hours after the last dosing, 3 μg/kg of norepinephirine was intravenously administered under pentobarbital sodium anesthesia (dosage 40 mg/kg; intraperitoneal) and the resulting pressor reaction was compared with that in the untreated control group.

Results

The results are shown in Table 5. It is apparent that although the application of the combination of the ointment base of this invention and the drug was a kind of percutaneous administration, it produced a drug effect (inhibition of pressor reaction) comparable to that of oral administration.

TABLE 5

| Pressor reaction (mmHg) | |
|---|---|
| Treatment group | Control |
| (B) 34.9 ± 2.2* | 48.6 ± 1.2 |
| (A) 36.3 ± 1.5* | 43.9 ± 1.5 |

*A significant difference from the control group with risk factor of 5%. (No significant difference between A and B groups)

* A significant difference from the control group with risk factor of 5%. (No significant difference between A and B groups)

TEST EXAMPLE 3

Percutaneous absorption of Indomethacin-containing preparation

Method

The indomethacin-containing ointment (2 g/body) of Example 4 containing 20 mg of indomethacin was applied onto the back of male albino rabbits (b. wt. 2.4–2.8 kg) clipped of hairs 24 hours before medication. During 0.5–7 hours following the application, 3 ml aliquots of blood were taken at timed intervals and the plasma separated by centrifugation was treated in accordance with the method of Arbin [J. Chromatog., 144, 85 (1977)] and assayed for indomethacin by mass fragmentography monitoring m/e 137 on a GC-MS apparatus (gas chromatography-mass spectrometer type QP-1000 Shimadzu Seisakusho Ltd.)

Results

The results are set forth in Table 6. It is apparent that the drug was absorbed from the skin quickly and sustainedly.

TABLE 6

| | Time (hr) | | | | |
|---|---|---|---|---|---|
| | 0.5 | 1 | 2 | 4 | 7 |
| Serum concentration of Indomethacin (ng/ml) | 24.9 | 22.3 | 13.6 | 14.7 | 8.1 |

TEST EXAMPLE 4

Percutaneous absorption of clonidine hydrochloride-containing preparation

Method

The clonidine hydrochloride-containing ointment (2 g/body) of Example 2 containing 10 mg of clonidine hydrochloride was applied onto the back of male albino rabbits (b. wt. 2.4–2.8 kg) clipped of hairs 24 hours before medication. 7 hours after application, the drug remaining on the skin was wiped off with sanitary cotton. During 0.5 to 24 hours following the application, 3 ml aliquots of blood were taken at timed intervals and the plasma separated by centrifugation was treated in accordance with the method of Edlund et al [Acta Pharmacol. Toxicol. 40, 145 (1977)] and assayed for clonidine by ECD-gas chromatography ($^{63}$Ni; Type GLC-4BM Shimadzu Seisakusho Ltd.).

Results

The results are set forth in Table 7. It is apparent that the drug was absorbed from the skin quickly and sustainedly.

TABLE 7

| | Time (hr) | | | | | |
|---|---|---|---|---|---|---|
| | 0.5 | 1.0 | 2.0 | 4.0 | 7.0 | 24.0 |
| Serum concentration of clonidine (ng/ml) | 24.7 | 32.2 | 16.9 | 13.9 | 4.7 | 1.2 |

TEST EXAMPLE 5

Drug release test of clonidine hydrochloride-containing preparation

Method

The ointments of Example 40-(a), (b) and (c) (each containing 0.1 weight percent of clonidine hydrochloride) and hydrophillic ointment described in the 10th revision of Japanese Pharmacopoeia (JPX) containing 0.1 weight percent of clonidine hydrochloride were used as the samples. Each 5 g of the above-mentioned samples were applied to the same equipment as used in Test Example 1. Thus 1 ml aliquots of the buffer were taken at timed intervals and 0.25 ml of 10% sodium carbonate were added to each aliquot which was then extracted with 5 ml of ethylacetate/dichloromethane mixed solution (1:9 by volume). The solvent was evaporated from the extract and the residue was dissolved in 0.3 ml of 75% acetonitrile to prepare an HPLC assay sample. The conditions of HPLC using the same equipment as in Test Example 1 were as follows: Column packing, Nucleosil® C18 (product of Macherey-Nagel, A.G. West Germany); Mobile phase, acetonitrile/1% acetic acid containing 0.005M 1-sodium heptane.sulfonate (40:50); flow rate, 1.2 ml/min; measurement by absorbance at UV frequency of 280 nm.

Results

The results are shown in Table 8.

TABLE 8

| | Release of clonidine (μg/ml) | | | | | |
|---|---|---|---|---|---|---|
| | Time (min) | | | | | |
| | 3 | 6 | 9 | 12 | 15 | 20 |
| Example 40 Ointment(a) | 0.9 | 1.6 | 2.1 | 2.6 | 2.9 | 3.6 |
| Example 40 Ointment(b) | 1.4 | 2.7 | 3.7 | 4.5 | 5.3 | 6.4 |
| Example 40 Ointment(c) | 1.2 | 2.0 | 2.5 | 2.8 | 3.4 | 3.9 |
| Hydrophillic ointment (JPX) | 0.2 | 0.3 | 0.3 | 0.4 | 0.5 | 0.5 |

The above results indicate that as compared with the above-mentioned hydrophillic ointment, the ointment base according to this invention ensures the better release of the drug.

TEST EXAMPLE 6

Percutaneous absorption of clidanac-containing preparation

Method

The ointment described in Example 50 containing 0.3 weight percent of clidanac and a publicly known ointment, i.e., ointment containing 0.5 weight percent of clidanac, described in the Japanese Kokai No. 59-48413, were used as samples. The publicly known ointment was a gel-like ointment containing no water-soluble protein which was prepared as follows: (1) 0.7 g of Hiviswako ® 104 and 0.7 g of hydroxy-cellulose were put in 30 g of purified water to be caused to swell (2) 0.5 g of clidanac was dissolved in the mixture of 12 g of butylene glycol, 1.5 g of diisopropyl adipate and 30 g of ethanol (3) the solution (2) was added to the mixture (1) and stirred until the contents are completely hydrated (4) 0.8 g of diisopropyl amine was dissolved in 10 g of purified water and the solution was added to the said mixture (3) and then the remaining water was added to make a total amount 100 g and the mixture was stirred to make total preparation homogenous, whereby the objective ointment was obtained.

The above-mentioned ointment was applied onto the back of male white rabbits,i.e. 3 to 4 rabbits each group, which were clipped of hairs for the area of 4×6 cm=24 cm$^2$ before medication. The dosage was set at 0.25 mg/kg in terms of clidanac. After application of the ointment, aliquots of blood were taken at timed intervals and assayed for the concentration of clidanac released into the serum (non-degenerated clidanac) by mass fragmentography.

Thus 1 ml aliquot of the above-mentioned serum was extracted twice with 5 ml of benzene/heptane mixture (2:1 by volume). The solvent of the first extract was evaporated and the residue was dissolved into the second extract. Thus obtained solution was extracted twice with 2.5 ml of dilute sodium hydroxide, dilute sulfuric acid was added to the aqueous layer to acidify and the solution was extracted twice with 3 ml of benzene. The internal standard substance was added to thus obtained extract, the solvent was evaporated and the residue was reacted with 2.2-dichloroethanol at 65° C. for 20 minutes under the presence of trifluoroacetic acid anhydride and the obtained derivative was assayed by MF method.

Results

The results are shown in Table 9.

TABLE 9

| Group | Serum concentration of clidanac (non-degenerated clidanac) (μg/ml) | | | | | | | AUC (ng · hr · ml$^{-1}$) |
| --- | --- | --- | --- | --- | --- | --- | --- | --- |
| | Time (min) | | | | | | | |
| | 15 | 30 | 60 | 120 | 240 | 360 | 480 | |
| Ointment of Example 50 | 5.2 | 8.5 | 9.4 | 13.1 | 15.1 | 16.0 | 16.7 | 110.1 |
| Publicly known ointment | 4.8 | 5.5 | 6.3 | 7.2 | 7.7 | 7.2 | 7.4 | 56.0 |

It is apparent from the above data that in comparison with the publicly known ointment, the ointment base of this invention displayed the performance to increase percutaneous absorption of the drug, and with less dosage it increased the bioavailability of the drug about twice.

TEST EXAMPLE 7

Serum concentration of pyroxycam-containing preparation

Method

Hairs on the back of male SD rats, i.e. 3 rats, body weight 250 to 325 g each group, were partially clipped off for the area of 3×3 cm=9 cm$^2$ and the below-mentioned specimens (A) and (B) were applied to the whole clipped area. The dosage was 0.5 mg/kg in terms of piroxicam.

(A) ointment containing piroxicam obtained in Example 43.

(B) publicly known ointment; an ointment containing piroxicam described in the Japanese Kokai No. 59-13714, which comprises the following components, 0.5 g piroxicam, 1.0 g of Hiviswako ® 105, 1.3 g of diisopropanol amine, 2 g of glycerin, 5 g of 1·3-butylene glycol, 30 g of ethanol and 60.2 g of purified water.

After dosing the above-mentioned samples (A) and (B), the serum concentration of piroxicam was assayed by fluorescent method (frequency 370 nm) according to the method described in the literature [Shichikawa et al, Rheumatism Vol 20, 214 (1980), published by Japan Rheumatism Society].

Results

The results are shown in Table 10.

TABLE 10

| Group | Serum concentration of piroxicam (μg/cm) | | | AUC (μg · hr · ml$^{-1}$) |
| --- | --- | --- | --- | --- |
| | Time (hr) | | | |
| | 3 | 6 | 12 | |
| Ointment of Example 43 | 0.03 | 0.25 | 0.06 | 1.43 |
| Publicly known ointment | 0.11 | 0.06 | 0.06 | 0.73 |

The above results shows that the ointment base of this invention indicates about 1.8 times as high AUC value as that of the publicly known ointment and thus brings an increase of percutaneous absorption of the drug.

We claim:

1. A method for providing superior percutaneous absorption of a drug or drugs on the skin surface characterized by applying an ointment containing:
   (1) one or two water soluble proteins for promoting percutaneous absorption of a drug or drugs and being selected from the group consisting of gelatin, casein and soybean protein, in a range of 0.5 to 30 weight % based on the weight of the whole ointment;
   (2) a monohydric alcohol having a carbon number of 2 to 4, in a range of 1 to 45 weight % based on the weight of the whole ointment;
   (3) one or two wetting agents selected from the group consisting of alkylene glycol containing 2 to 6 carbon atoms, polyethylene glycol having average molecular weight of about 200 to 800, glycerin, trimethylolpropane and sorbitol, in a range of 1 to 35 weight % based on the weight of the whole ointment; and
   (4) a drug or drugs absorbed percutaneously in a range of 0.01 to 15 weight % based on the weight of the whole ointment.

2. A method as claimed in claim 1, said ointment further containing water in a range of from 20 to 50 weight %.

3. A method as claimed in claim 1, said ointment further containing cellulose derivative, polysaccharide, carboxyvinyl polymer, polyvinyl alcohol or polyvinylpyrrolidone in an amount ranging from about 0.1 to 10 weight %; said cellulose derivative being alkyl cellulose or hydroxy alkyl cellulose having an average molecular weight in the range of about 40,000 to 200,000 and an alkyl moiety containing 1 to 4 carbon atoms.

4. A method as claimed in claim 1, said ointment further containing nonionic, anionic or cationic surfactant in an amount ranging from about 0.1 to 5 weight %.

5. A method as claimed in claim 1, wherein the monohydric alcohol is ethanol.

6. A method as claimed in claim 1, said ointment further containing paraben in an amount of about 0.05 to 2 weight %.

7. A method as claimed in claim 1, said ointment further containing organic acid, inorganic acid, alkali metal salt of organic acid or alkali metal salt of inorganic acid in an amount of from about 0.1 to 5 weight %.

8. A method as claimed in claim 1, said ointment further containing one to four oleoginous substances selected from the group consisting of isopropyle myristate, octyldodecyl myristate, myristyl myristate, isopropyl palmitate, butyl stearate, decyl oleate, diisopropyl adipate, diethyl sebacate, hexyldecyl dioctate, sorbitan monopalmitate, saccharose fatty acid ester, triacetin, di- or triglyceride caprylate, di- or triglyceride caprate, mixed trigriceride comprising caprylic acid and capric acid, di- or triglyceride oleate, di- or triglyceride linolate, mixed glyceride comprising oleic acid and linolic acid, cetanol, palmityl alcohol, stearyl alcohol, oleyl alcohol, hexadecyl alcohol, paraffin oil, lanolin oil and silicone oil in a range of from 0.5 to 30 weight % based on the weight of the whole ointment base.

* * * * *